United States Patent
Hoernig

(10) Patent No.: US 8,855,745 B2
(45) Date of Patent: Oct. 7, 2014

(54) MAMMOGRAPHY INSTALLATION

(75) Inventor: Mathias Hoernig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 165 days.

(21) Appl. No.: 13/432,325

(22) Filed: Mar. 28, 2012

(65) Prior Publication Data

US 2012/0253187 A1    Oct. 4, 2012

(30) Foreign Application Priority Data

Mar. 29, 2011 (DE) .......................... 10 2011 006 353

(51) Int. Cl.
*A61B 6/04* (2006.01)
*A61B 6/00* (2006.01)
*A61B 6/03* (2006.01)

(52) U.S. Cl.
CPC ............ *A61B 6/032* (2013.01); *A61B 6/482* (2013.01); *A61B 6/0435* (2013.01); *A61B 6/4014* (2013.01)
USPC ........................................ 600/431; 600/458

(58) Field of Classification Search
USPC ........................................................ 600/431
See application file for complete search history.

(56) References Cited

U.S. PATENT DOCUMENTS

| | | | |
|---|---|---|---|
| 6,480,565 B1 * | 11/2002 | Ning | 378/37 |
| 7,558,367 B1 * | 7/2009 | Tinwala et al. | 378/37 |
| 7,702,066 B2 * | 4/2010 | Boyden et al. | 378/45 |
| 7,945,019 B2 | 5/2011 | Kalender et al. | |
| 2009/0129556 A1 * | 5/2009 | Ahn | 378/208 |
| 2010/0290585 A1 | 11/2010 | Eliasson | |

FOREIGN PATENT DOCUMENTS

| | | |
|---|---|---|
| DE | 199 05 239 | 8/2000 |
| DE | 100 26 792 | 12/2001 |

* cited by examiner

*Primary Examiner* — Tse Chen
*Assistant Examiner* — Lisa Kinnard
(74) *Attorney, Agent, or Firm* — Schiff Hardin LLP

(57) ABSTRACT

A mammography installation or a mammography system allows x-ray projections of the breasts for at least one 3D volume image to be calculated with and without a contrast agent progression, and without repositioning of the patient within an examination cycle.

5 Claims, 3 Drawing Sheets

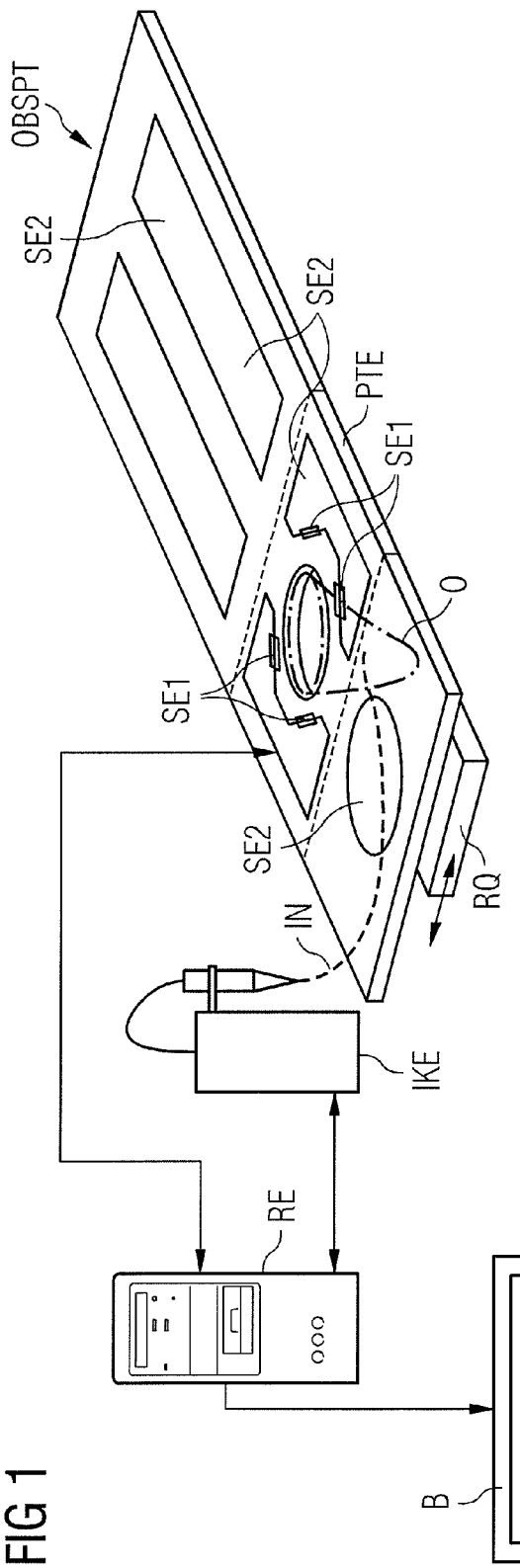

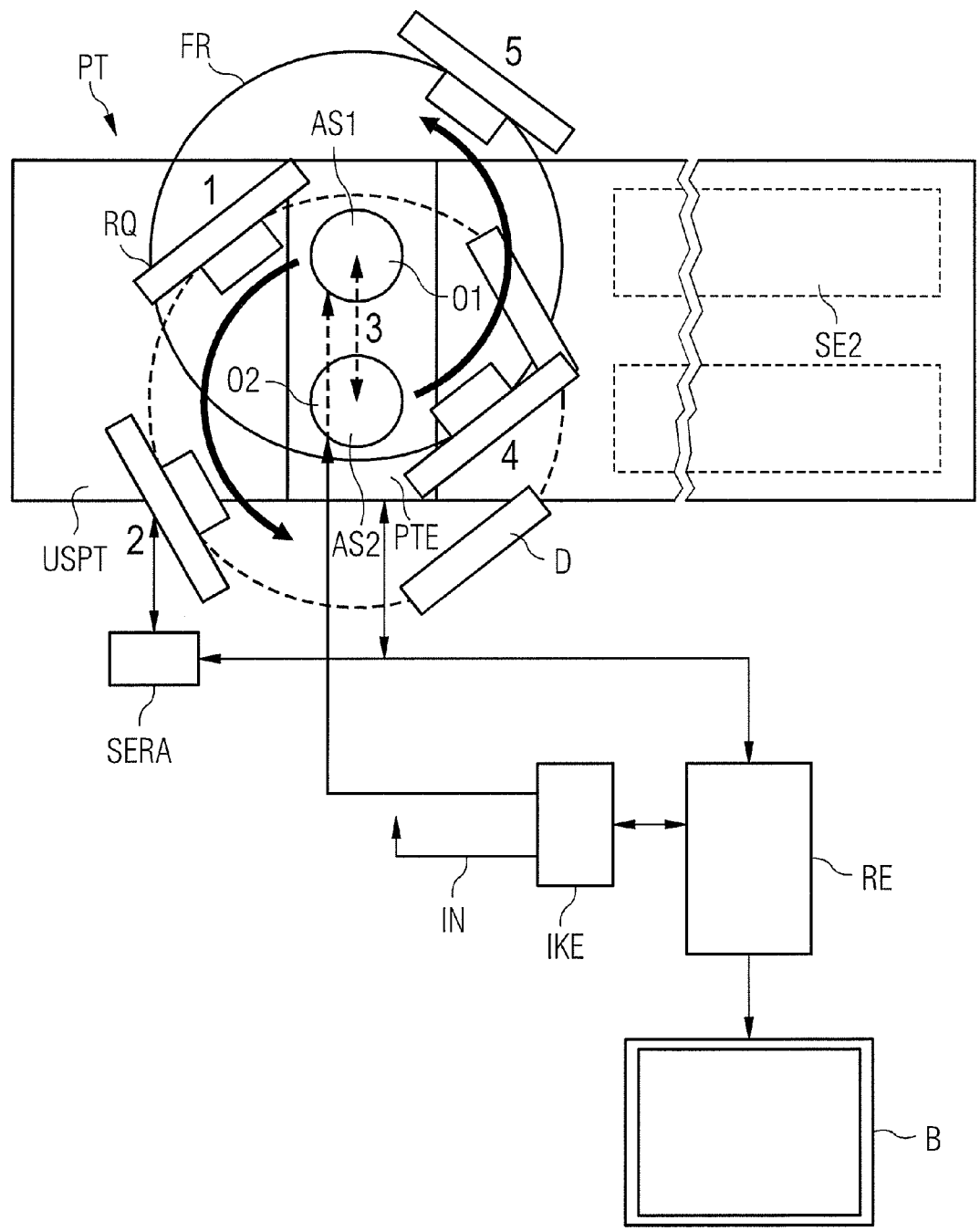

MAMMOGRAPHY INSTALLATION

BACKGROUND OF THE INVENTION

1. Field of the Invention

The present invention concerns a mammography installation or a mammography system of the type wherein the patient lies prone on a bed surface of a bed arrangement while x-ray images of the breast of the patient are generated.

2. Description of the Prior Art

In digital contrast agent mammography, differentiation is made between digital dynamic subtraction mammography and dual energy subtraction mammography.

In digital dynamic subtraction mammography, a reference or baseline exposure of the breast is produced by means of a digital mammography system. After a contrast agent injection, multiple contrast agent exposures are subsequently produced at predeterminable time intervals from exactly the same position. These are logarithmically subtracted from the blank exposure so that the contrast agent enrichment is visible.

In the temporary dual energy subtraction method, two x-ray exposures with respectively different photon energies are produced after the administration of a contrast agent comprising iodine, wherein the energy magnitudes of both radiation beams border the K-edge of iodine. Since the absorption properties differ due to the different energy magnitudes, after equalizing the exposure level and subsequent weighted, logarithmic subtraction of the two x-ray exposures, a contrast agent enrichment can likewise be presented.

For example, in the case of a digital, full-field mammogram (FFDM), one or more digital x-ray exposures are made of the respective breast after a respective repositioning of the patient, before the use of a contrast agent. Additional x-ray exposures of breast tissue are subsequently produced with contrast agent, respectively with a new repositioning of the patient. However, the generation of x-ray exposures of both breasts has the disadvantage that x-ray exposures of each breast must be generated separately. This extra time expenditure is accompanied by an increased physical stress due to the administration of contrast agent.

SUMMARY OF THE INVENTION

An object of the present invention is to provide a mammography system in which the disadvantages cited above are avoided.

The above object is achieved in accordance with the present invention by a mammography installation having a patient bed unit with a first recess therein that is configured to allow at least one breast to be located therein when a patient lies in a prone position on the bed unit, a contrast agent injector unit, and an x-ray unit having at least one x-ray source and a radiation detector located below the bed unit so as to irradiate at least one breast of the patient that proceeds through the recess. At least one sensor element is provided that detects the prone behavior of the patient and emits a signal as long as the patient remains in the prone position with at least one breast in the recess. The signal is supplied to a control unit that is configured to automatically interrupt a mammography procedure being conducted using the x-ray unit if it is detected that the patient has moved out of the prone position. The x-ray source, moreover, is selectively controlled to operate with a first supply voltage or a second, higher supply voltage in order to obtain images before and after injection of contrast agent by the contrast agent injector.

The invention has the advantage that the patient does not need to be relocated or repositioned given a mammogram of both breasts.

The invention also has the advantage that the x-ray system of the mammography installation is designed such that this is centered with respect to the examination subject.

The invention has the further advantage that a double repositioning is omitted for the generation of x-ray images for both breasts according to dual energy imaging.

The invention also has the advantage that different angle ranges can be covered for the tomoscan.

The invention also has the advantage that a 4D imaging with take-up/wash-out can be visualized on a monitor.

BRIEF DESCRIPTION OF THE DRAWINGS

FIG. 1 schematically illustrates a mammography installation that can be used to implement the invention.

FIG. 2 shows an embodiment of a bed unit associated with the mammography installation.

FIG. 3 shows an additional embodiment of the bed unit.

DESCRIPTION OF THE PREFERRED EMBODIMENTS

Figure 4:
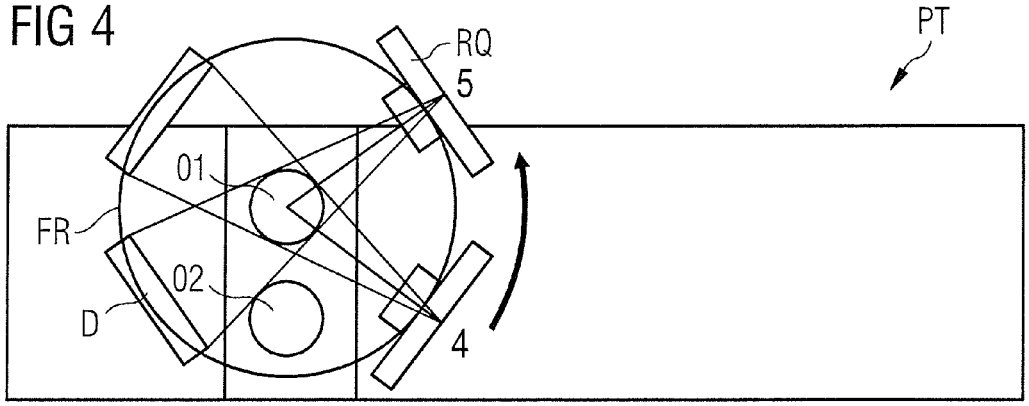
FIGS. 4, 5 and 6 illustrate setup of an associated x-ray unit.

If a series of x-ray exposures of breast tissue is respectively generated, a spatial resolution of a breast can thus be considered with a contrast agent progression in the glandular tissue of the respective breast after calculating the present digital x-ray image data. If a second series of x-ray exposures is generated under the influence of a contrast agent in temporary dual energy subtraction mammography, the kinetics of the take-up of the contrast agent in a lesion and the wash-out from the lesion are visible due to different absorption properties of the malignant versus healthy tissue in the breast.

To evaluate slice images after a tomosynthesis has been implemented, given a use of contrast agent its distribution or concentration in the glandular tissue of the respective breast can additionally be worked out.

The basis of the invention is to design mammography installations or mammography systems such that a repositioning is not required in the case of spiral CT, cone beam CT or FFDM CT, for example, in particular with a ventral positioning of the patient.

A mammography installation is schematically shown in FIG. 1. For clarity, the basic components of the mammography installation are: a bed unit Patent and Trademark Office, an x-ray unit composed of an x-ray source RQ and a detector D, a contrast agent injector unit IKE, and a computer RE with an associated visualization unit B. The bed unit PT—which can also be designated as a prone table—has bed elements on which the patient lies prone while the x-ray exposures are generated. A bed element PTE that can be exchanged (inserted) in the chest region of the bed surface of the bed unit PT is designed to have a first recess AS1 and a second recess AS2 in the chest region, depending on the scope of the examination. The recesses AS1, AS2 can be adapted to the breast size. The bed element PTE can also be designed such that only one recess AS is provided for both breasts. With insertion of the bed element PTE, the computer is signaled via contact elements at the bed element PTE as to whether exposures of one breast or both breasts are to be generated. First and/or second sensor elements SE1, SE2 are integrated on the top side OBPST of the bed unit PT. The first sensors SE1 that select the individual breast and deliver data for a respective virtual breast axis are arranged along the recesses on the bed element PTE at the edge region. The respective virtual breast axis is determined in the associated computer RE. Resistance, pressure, heat or capacitive sensors that signal contact with the body surface at the bed elements can also be arranged below the first sensors SE1 in the edge region of the recesses. The density of the second sensors SE2 integrated into the bed unit PT is increased in the leg, chest and head region. The prone posture of the patient can be detected by these sensor elements SE1, SE2. If no sufficient feedback with regard to pressure loading takes occurs from the sensor elements in the region of the recess for the breast, or an insufficient detection of the skin resistance exists, or only a punctiform or one-sided loading of the surface of the bed exists, the triggering of an x-ray acquisition is carefully stopped or the x-ray acquisition cycle is interrupted after exceeding a predetermined threshold.

The x-ray unit with at least one x-ray source RQ and a detector unit D is arranged below the bed PT. Both a singular x-ray source RQ and a multifocus tube can be used as an x-ray source RQ. The x-ray source RQ can be moved by means of step motors or manually shifted below the bed PT, corresponding to the scope of the examination.

A computer RE is similarly schematically indicated in FIG. 1. The computer RE, evaluates the prone posture of the patient and the x-ray system is controlled accordingly, and the x-ray images read out from the detector unit D are processed into volume images. The examination progress can be displayed by mean of the computer RE, and the 3D images created by the computer RE can be depicted separately or with a time curve of the contrast agent concentration in the tissue of the breast. The computer RE controls the contrast agent injector unit IKE for the injection of a contrast agent dependent on the patient data, depending on the respective acquisition cycle. In this embodiment of the invention, the breast is not compressed before the x-ray acquisition. In a further embodiment variant, the breast or breasts could be fixed with a compression unit. In order to ensure that the tissue of the breast does not experience any spatial displacement during the x-ray acquisitions, as described above sensor elements SE1, SE2 are integrated into the bed unit. For example, if the patient moves on the bed, pressure is exerted on the sensor elements. The sensor signals are evaluated by the computer RE. If the pressure signals acquired at points by the sensor elements exceed a predetermined threshold, the computer RE generates a stop signal for the x-ray system. The triggering of x-ray images is temporarily interrupted. If the patient settles down and this is confirmed by sensor signals received by the computer RE, the acquisition of the x-ray images or the examination program is continued.

The bed unit or the prone table PT is fashioned in the chest region with a bed element PTE through which either one breast or both breasts proceed during an examination cycle (for example a dual energy examination cycle) without repositioning of the patient. The shape of the bed element PTE is respectively signaled to the computer RE via sensors or contact elements integrated into said bed element PTE. The x-ray system is controlled corresponding to the shape of the bed element PTE, and the contrast agent injector unit IKE is initialized such that the contrast agent is injected into a vein of the patient (for example) after a native acquisition cycle.

In FIG. 2 the shape of the bed or the prone table PT is depicted in an embodiment variant. In this embodiment, an x-ray image presentation of both breasts is intended. For this, before the x-ray image cycles a bed element PTE with two openings is inserted into the bed unit PT. Upon insertion of the bed element PTE, the x-ray source and the associated detector are automatically set to be centered on a first examination subject O to be established (for example the right breast O2), based on contact elements at the bed element PTE. In this embodiment, among other things first and second sensor elements SE1, SE2 are integrated into the surface of the central bed element PTE. By means of these and additional second sensor elements SE2 arranged in the leg region, how the patient is lying on the bed PT during an x-ray acquisition cycle is signaled to a sensor program in the computer. An x-ray source RQ and an associated detector unit D are also schematically depicted in FIG. 2. Given a correspondingly designed multifocus tube, x-ray exposures of both breasts could be generated during an x-ray acquisition cycle.

The underside of a bed unit PT is schematically depicted in FIG. 3. In this embodiment variant, at least one x-ray source RQ and a detector unit D opposite this x-ray source are arranged on an annular guide element FR, for example. The orientation of the guide ring and the x-ray unit arranged on it is controlled by the computer RE and a control module SERA. Level adaptations for control motors to align the x-ray source and/or the detector unit are likewise implemented with the control module SERA. Depending on the embodiment of the bed element PTE, the guide element can be displaced horizontally. In a further embodiment, the guide element FR can also be fashioned in the form of a circle segment. When located in the rest position, the guide element FR is aligned centrally below the bed element PTE. For example, if a central bed element PTE with first and second recesses AS1, AS2 for an examination cycle with two breasts is now inserted into the bed unit PT, the guide element FR travels horizontally in the direction of first or second recess AS1, AS2 corresponding to a pre-established examination sequence. The guide element FR is positioned centrally relative to the respective recess. The control signals for this are generated in the computer, for example, and in the control unit SERA provided for the x-ray system. For example, if the process begins with an x-ray acquisition of the right breast O2, the guide element FR travels horizontally to the second recess AS2 provided for the right breast O2 until the guide element FR is positioned centrally relative to this. As is indicated in FIG. 3, the x-ray acquisitions begin with a first x-ray acquisition at position 1. The x-ray acquisition cycle ends with the x-ray source RQ at position 2. The guide element FR is subsequently shifted vertically and horizontally to the first recess AS1 and positioned centrally relative to this. The second x-ray acquisition cycle is begun with a first x-ray acquisition at position 4, and the x-ray acquisition cycle with regard to the left breast is ended with the x-ray source RQ at position 5. Both x-ray image sequences are respectively processed into a respective volume image (for example) in the computer RE. Both volume images can be shown jointly or individual on a monitor unit. A contrast agent injection takes place specific to the patient. Because the x-ray acquisition procedure of the first and second x-ray acquisition cycle can be temporally defined, the contrast agent can be administered to the patient in a patient-specific manner. The contrast agent enrichment in the breast should already have begun when the respective third or fourth x-ray acquisition cycle begins. The x-ray exposures of the third or fourth x-ray acquisition cycle are acquired with application of a second (i.e. higher) x-ray voltage. The injection of contrast agent takes place via the contrast agent injector unit IKE and the injection lines IN that are provided for this purpose. Alternatively, a 2D acquisition can take place at predeterminable angles or within a reduced angle range. X-ray image evaluations can be diagnosed at the monitor connected to the computer RE. In the following are the method steps for the dual energy x-ray scan, with a first through fourth x-ray image cycle:

In a first step, first sensors SE1 are polled to detect the breasts and first and second sensors SE1, SE2 are polled to monitor the prone behavior. For this the measurement data of the first and second sensors SE1, SE2 are relayed continuously to the respective processing units of the computer RE are polled by these during the x-ray image cycles. If the patient rests on the bed surface of the bed unit PT without movement, the x-ray acquisitions of an x-ray acquisition cycle are started or continuously implemented.

In a second step, the guide element FR is aligned relative to a first breast O1 such that this is positioned in the center of the guide ring FR and the x-ray unit (comprising x-ray source RQ and associated detector unit D) arranged on it is brought into a start position. The guide ring FR can also be moved vertically before the x-ray acquisitions are begun or during the x-ray acquisition cycle.

In a third step, the x-ray system starts a first x-ray acquisition cycle of the second breast O2 with application of a first x-ray supply voltage (i.e. low x-ray voltage) to the x-ray source RQ. X-ray exposures of the first breast O1 are generated during a second x-ray acquisition cycle after movement and positioning of the guide ring FR while maintaining the first x-ray supply voltage.

In a fourth step, a second x-ray supply voltage for additional x-ray scans is applied to the x-ray source RQ. The second x-ray supply voltage has a higher voltage potential depending on the contrast agent that is used. Depending on the patient, the contrast agent is still injected into the patient during or at the end of the second x-ray acquisition cycle since between a couple of seconds and a minute passes until an enrichment of the contrast agent in the mamma (this is specific to the patient). After the third x-ray acquisition cycle of the first breast O1, a fourth x-ray acquisition cycle takes place immediately after the alignment of the guide ring FR at the second breast O2.

Alternatively, instead of a third and fourth x-ray scan a 2D high-kV x-ray acquisition can respectively take place at a predeterminable angle, or a scan can take place at a reduced angle range (for example +/−5 degrees).

In a further embodiment, low-energy exposures can be generated in a continuous scan for the first and second breast and high-energy exposures can be generated in an additional continuous scan. The guide element FR is directed in a rotation and translation movement from the first breast to the second breast or from the second breast to the first breast. The movement of the x-ray source and of the detector around the first and second breast can likewise take place in such a manner that the x-ray source and the detector travel on the guide element FR around the breast, and the guide element FR is directed in a rotation and/or translation motion for the change between the breasts.

In a fifth step, the x-ray images of the first through fourth x-ray image acquisition cycle of the first and second subject O1, O2 are calculated into volume images 3D, and the slice images with and/or without use of contrast agent are presented at the monitor unit B.

In an embodiment of the mammography installation with a multifocus tube, this can extend over the entire width of the bed unit. An associated detector can be moved behind the second subject after exposure of the first subject. In a further embodiment, the multifocus tube is part of the previously described multifocus tube. After a first scan of the first subject O1, the multifocus tube is then driven to a second scan of the second subject O2.

Figure 5:
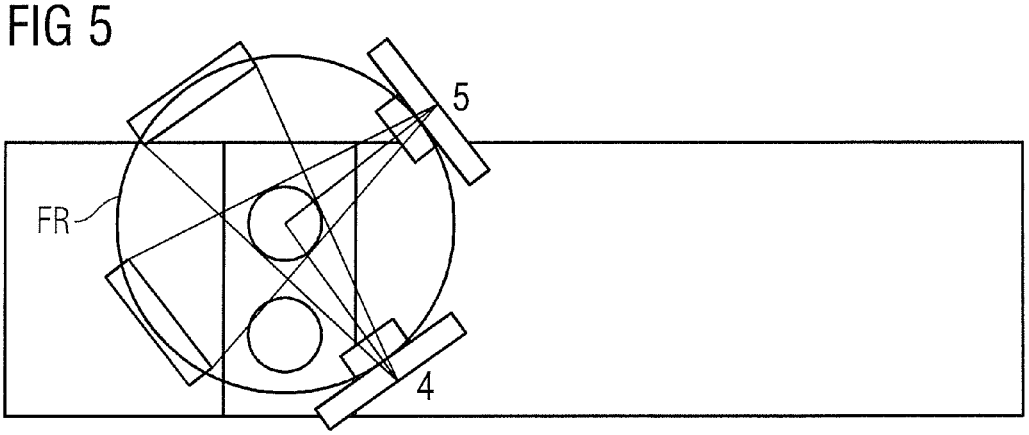
Figure 6:
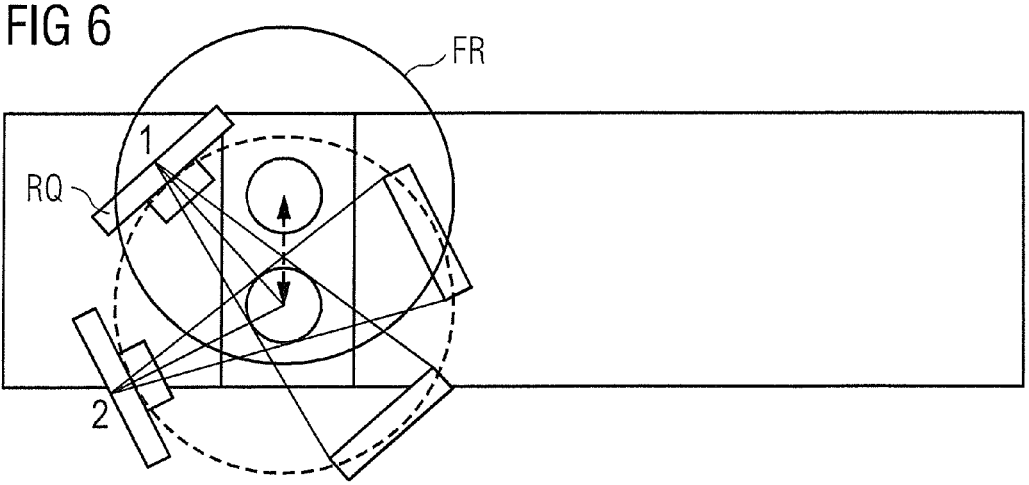

Respective positions of the guide ring FR with x-ray source RQ and detector unit D are shown in FIGS. 4, 5 and 6.

FIG. 4 shows a method segment from the mammography installation shown in FIG. 3. In this method segment, x-ray exposures of the left breast O1 are created with an x-ray source RQ supplied with low energy. A number of x-ray images of the right breast O1 are acquired by means of a low-energy tomoscan. This begins at position 4 of the x-ray source RQ.

The same method segment as in FIG. 4 is reproduced in FIG. 5 for an expanded angle range.

The method segment with regard to the low-energy tomoscan for the right breast is indicated in FIG. 6. For this purpose, as described with regard to FIG. 3 the guide element FR is shifted into a guide plane until the right breast is centered within the guide element FR.

Although modifications and changes may be suggested by those skilled in the art, it is the intention of the inventor to embody within the patent warranted hereon all changes and modifications as reasonably and properly come within the scope of his contribution to the art.

I claim as my invention:

1. A mammography installation comprising:
    a bed unit configured to receive a patient thereon in a prone position, said bed unit having recesses therein configured to allow breasts of the patient to proceed through the recesses when the patient is in the prone position on the bed unit;
    a contrast agent injector adapted to administer contrast agent to the patient on the bed unit;
    an x-ray imaging unit located at a central position beneath the patient bed between said recesses, and comprising an x-ray source and a radiation detector configured to irradiate a breast in a respective recess to obtain a set of x-ray projections of the breast in the respective recess;
    a sensor that detects whether said patient is in said prone position on said bed unit and that emits an output signal as long as said patient remains in said prone position on the bed unit;
    a control unit provided with said sensor output signal, said control unit being configured to operate said x-ray imaging unit and to interrupt operation of said x-ray unit when said sensor output signal indicates the patient is not in said prone position;
    said control unit being configured to operate said x-ray imaging unit and said contrast agent injector according to an imaging protocol that defines an imaging sequence in which said set of x-ray projections is acquired from a first of said breasts prior to acquiring said set of x-ray projections from a second of said breasts;
    said control unit, dependent on said imaging protocol, being configured to automatically move said x-ray unit from said central position to a position for acquiring said set of x-ray projections from said first of said breasts and thereafter to automatically move said x-ray imaging unit to a position for acquiring said set of x-ray projections from said second of said breasts;
    said control unit being configured to operate said x-ray imaging unit and said contrast agent injector in said imaging protocol to acquire the respective set of x-ray projections of at least one of the breasts as a contrast-enhanced set of x-ray projections by operating said x-ray source with a first supply voltage, timed relative to administration of said contrast agent to the patient, to obtain at least one of said x-ray projections of said at least one breast in said recess prior to injection of said contrast agent by said contrast agent injector, and to operate said x-ray source with a second supply voltage, that is higher than said first supply voltage, to obtain at least one additional one of said x-ray projections of said at least one breast in said recess after injection of contrast agent by said contrast agent injector; and said control unit comprising a processor supplied with the respective sets of projections of the respective breasts, and said processor being configured to reconstruct a 3D image data set of each of said breasts from the respective sets of 2D projections, with said 3D image data set for said at least one of said breasts being a contrast-enhanced 3D image data set, and said processor being configured to provide said 3D image data sets to a display to cause respective images of the breasts to be shown at said display.

2. A mammography installation as claimed in claim 1 wherein said sensor element is a first sensor element, and comprising a second sensor element in said bed unit that also monitors said prone behavior of the patient on the bed unit that provides a second sensor output to said control unit.

3. A mammography installation as claimed in claim 1 wherein said recesses configured to allow both breasts of the patient to proceed through the recess, and wherein said sensor element detects whether one or both breasts are present in said recess, and wherein said control unit is configured to operate said x-ray source dependent on detection by said sensor element of one or both breasts in said recess.

4. A mammography installation as claimed in claim 1 wherein said at least sensor element is a contact sensor that detects physical contact with said patient on said bed unit.

5. A mammography method comprising:
placing a patient in a prone position on a bed unit, said bed unit having recesses therein configured to allow breasts of the patient to proceed through the recesses when the patient is in the prone position on the bed unit, and an x-ray imaging unit located at a central position beneath the patient bed between said recesses, and comprising an x-ray source and a radiation detector configured to irradiate a breast in a respective recess to obtain a set of x-ray projections of the breast in the respective recess;
connecting the patient to a contrast agent injector adapted to administer contrast agent to the patient on the bed unit;
with a sensor detecting whether said patient is in said prone position on said bed unit and emitting an output signal from said sensor as long as said patient remains in said prone position on the bed unit;
supplying said sensor output signal to a control unit provided and, from said control unit, operating said x-ray imaging unit and to interrupt operation of said x-ray unit when said sensor output signal indicates the patient is not in said prone position;
from said control unit, operating said x-ray imaging unit and said contrast agent injector according to an imaging protocol that defines an imaging sequence in which said set of x-ray projections is acquired from a first of said breasts prior to acquiring said set of x-ray projections from a second of said breasts;
from said control unit, dependent on said imaging protocol, automatically moving said x-ray unit from said central position to a position for acquiring said set of x-ray projections from said first of said breasts and thereafter automatically moving said x-ray imaging unit to a position for acquiring said set of x-ray projections from said second of said breasts;
from said control, unit operating said x-ray imaging unit and said contrast agent injector in said imaging protocol to acquire the respective set of x-ray projections of at least one of the breasts as a contrast-enhanced set of x-ray projections by operating said x-ray source with a first supply voltage, timed relative to administration of said contrast agent to the patient, to obtain at least one of said x-ray projections of said at least one breast in said recess prior to injection of said contrast agent by said contrast agent injector, and to operate said x-ray source with a second supply voltage, that is higher than said first supply voltage, to obtain at least one additional one of said x-ray projections of said at least one breast in said recess after injection of contrast agent by said contrast agent injector; and
in a processor supplied with the respective sets of projections of the respective breasts, reconstructing a 3D image data set of each of said breasts from the respective sets of 2D projections, with said 3D image data set for said at least one of said breasts being a contrast-enhanced 3D image data set, and providing said 3D image data sets to a display to cause respective images of the breasts to be shown at said display.

* * * * *